United States Patent
Yoda

(10) Patent No.: US 12,390,182 B2
(45) Date of Patent: Aug. 19, 2025

(54) X-RAY CT APPARATUS, X-RAY CT APPARATUS CONTROL METHOD, AND STORAGE MEDIUM

(71) Applicant: CANON MEDICAL SYSTEMS CORPORATION, Otawara (JP)

(72) Inventor: Takahiro Yoda, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 288 days.

(21) Appl. No.: 17/809,149

(22) Filed: Jun. 27, 2022

(65) Prior Publication Data

US 2022/0409162 A1    Dec. 29, 2022

(30) Foreign Application Priority Data

Jun. 29, 2021 (JP) ................................. 2021-107643

(51) Int. Cl.
- *A61B 6/00* (2024.01)
- *A61B 6/03* (2006.01)
- *G06T 11/00* (2006.01)

(52) U.S. Cl.
CPC .............. *A61B 6/541* (2013.01); *A61B 6/032* (2013.01); *A61B 6/4435* (2013.01); *G06T 11/005* (2013.01)

(58) Field of Classification Search
CPC ......... A61B 6/032; A61B 6/06; A61B 6/4035; A61B 6/4435; A61B 6/503; A61B 6/541; G06T 11/005
See application file for complete search history.

(56) References Cited

U.S. PATENT DOCUMENTS

| | | | | |
|---|---|---|---|---|
| 4,654,797 A | * | 3/1987 | Fujita | ................. G06T 11/006 378/901 |
| 5,751,782 A | * | 5/1998 | Yoshitome | ............. A61B 6/032 378/98.5 |

(Continued)

FOREIGN PATENT DOCUMENTS

| JP | 60-138680 A | 7/1985 |
|---|---|---|
| JP | 2004-356 A | 1/2004 |

(Continued)

OTHER PUBLICATIONS

Japanese Office Action issued Dec. 10, 2024 in Japanese Patent Application No. 2021-107643, 5 pages.

*Primary Examiner* — David J Makiya
*Assistant Examiner* — Soorena Kefayati
(74) *Attorney, Agent, or Firm* — Oblon, McClelland, Maier & Neustadt, L.L.P.

(57) ABSTRACT

An X-ray CT apparatus of an embodiment acquires projection data of a subject based on X-ray detection data according to biometric information synchronous scanning and generates a CT image of the subject based on the projection data. The X-ray CT apparatus includes a first acquisition unit, a determination unit, and a second acquisition unit. The first acquisition unit acquires biometric information of the subject at a timing when the biometric information synchronous scanning has been performed. The determination unit determines, as priority data, detection data that is a target for which data transfer will be preferentially performed among X-ray detection data acquired in the biometric information synchronous scanning based on the biometric information. The second acquisition unit acquires the priority data from a storage device that holds the detection data.

9 Claims, 10 Drawing Sheets

(56) References Cited

U.S. PATENT DOCUMENTS

| | | | |
|---|---|---|---|
| 2005/0175143 A1* | 8/2005 | Miyazaki | A61B 6/032 378/19 |
| 2008/0221442 A1* | 9/2008 | Tolkowsky | A61B 6/5217 378/22 |
| 2009/0060120 A1* | 3/2009 | Mukumoto | A61B 6/503 378/8 |
| 2014/0254762 A1* | 9/2014 | Yamato | A61B 6/541 378/62 |
| 2014/0328462 A1* | 11/2014 | Uehara | A61B 6/5288 378/62 |
| 2015/0139388 A1* | 5/2015 | Liu | A61B 6/503 378/62 |
| 2016/0345926 A1* | 12/2016 | Dutta | A61B 6/032 |
| 2017/0086771 A1* | 3/2017 | Yasuhiro | G16H 50/30 |
| 2017/0196527 A1* | 7/2017 | Kokubun | A61B 6/5217 |
| 2018/0276854 A1* | 9/2018 | Suzuki | G01N 23/046 |
| 2018/0330502 A1* | 11/2018 | Ikeda | A61B 6/541 |
| 2019/0150857 A1* | 5/2019 | Nye | G16H 30/40 |
| 2019/0192104 A1* | 6/2019 | Thran | A61B 5/352 |

FOREIGN PATENT DOCUMENTS

| | | |
|---|---|---|
| JP | 2007-315 A | 1/2007 |
| JP | 2009-240571 A | 10/2009 |
| JP | 2019-93137 A | 6/2019 |

* cited by examiner

X-RAY CT APPARATUS, X-RAY CT APPARATUS CONTROL METHOD, AND STORAGE MEDIUM

CROSS-REFERENCE TO RELATED APPLICATION

The present application claims priority based on Japanese Patent Application No. 2021-107643 filed Jun. 29, 2021, the content of which is incorporated herein by reference.

BACKGROUND

Field

Embodiments disclosed herein relate generally to an X-ray CT apparatus, an X-ray CT apparatus control method, and a storage medium.

Conventionally, there is an X-ray computed tomography (CT) apparatus that generates a cross-sectional image of a subject using X-rays. As X-ray CT apparatuses, one that collects and transfers projection data in parallel and one that acquires projection data and then transfers the acquired projection data are known. Although the latter method (hereinafter referred to as "two-stage transfer method") was devised because real-time data transfer became difficult with the former method due to increases in capacity of projection data, it takes more time to complete data transfer than the former method. In recent years, an X-ray CT apparatus capable of generating a cross-sectional image that is less affected by movement of a subject according to electrocardiographic synchronous scanning for acquiring projection data at a timing when movement of the subject is small based on electrocardiographic waveforms of the subject has also been developed.

However, a long time is required for the two-stage transfer type X-ray CT apparatus. Furthermore, when helical scanning is performed as electrocardiographic synchronous scanning, a helical pitch needs to be shorter than that of normal helical scanning in order to guarantee reconstruction at all phases, which increases the amount of data to be acquired and requires more time for data transfer. For this reason, when electrocardiographic synchronous scanning in a two-stage transfer type X-ray CT apparatus is performed, a time required for acquisition and transfer of projection data increases, and reconstruction processing at a target phase cannot be performed immediately after examination is completed and thus there is a possibility that it will take a long time to determine success or failure of examination.

DETAILED DESCRIPTION

Hereinafter, an X-ray CT apparatus, an X-ray CT apparatus control method, and a storage medium of embodiments will be described with reference to the drawings.

An X-ray CT apparatus of an embodiment is an apparatus that acquires projection data of a subject based on X-ray detection data according to biometric information synchronous scanning and generates a CT image of the subject based on the projection data. The X-ray CT apparatus includes a processing circuitry. The processing circuitry acquires biometric information of the subject at a timing when the biometric information synchronous scanning has been performed. The processing circuitry determines, as priority data, detection data that is a target for which data transfer will be preferentially performed among X-ray detection data acquired in the biometric information synchronous scanning based on the biometric information. The processing circuitry acquires the priority data from a storage device that holds the detection data.

An X-ray CT apparatus of an embodiment is an apparatus that acquires projection data of a subject based on X-ray detection data according to biometric information synchronous scanning and generates a CT image of the subject based on the projection data. The X-ray CT apparatus includes a processing circuitry. The processing circuitry acquires exposure information indicating an X-ray exposure timing in the biometric information synchronous scanning. The processing circuitry determines, as priority data, detection data that is a target for which data transfer will be preferentially performed among X-ray detection data acquired in the biometric information synchronous scanning based on the exposure information. The processing circuitry acquires the priority data from a storage device that holds the detection data.

First Embodiment

Figure 1:
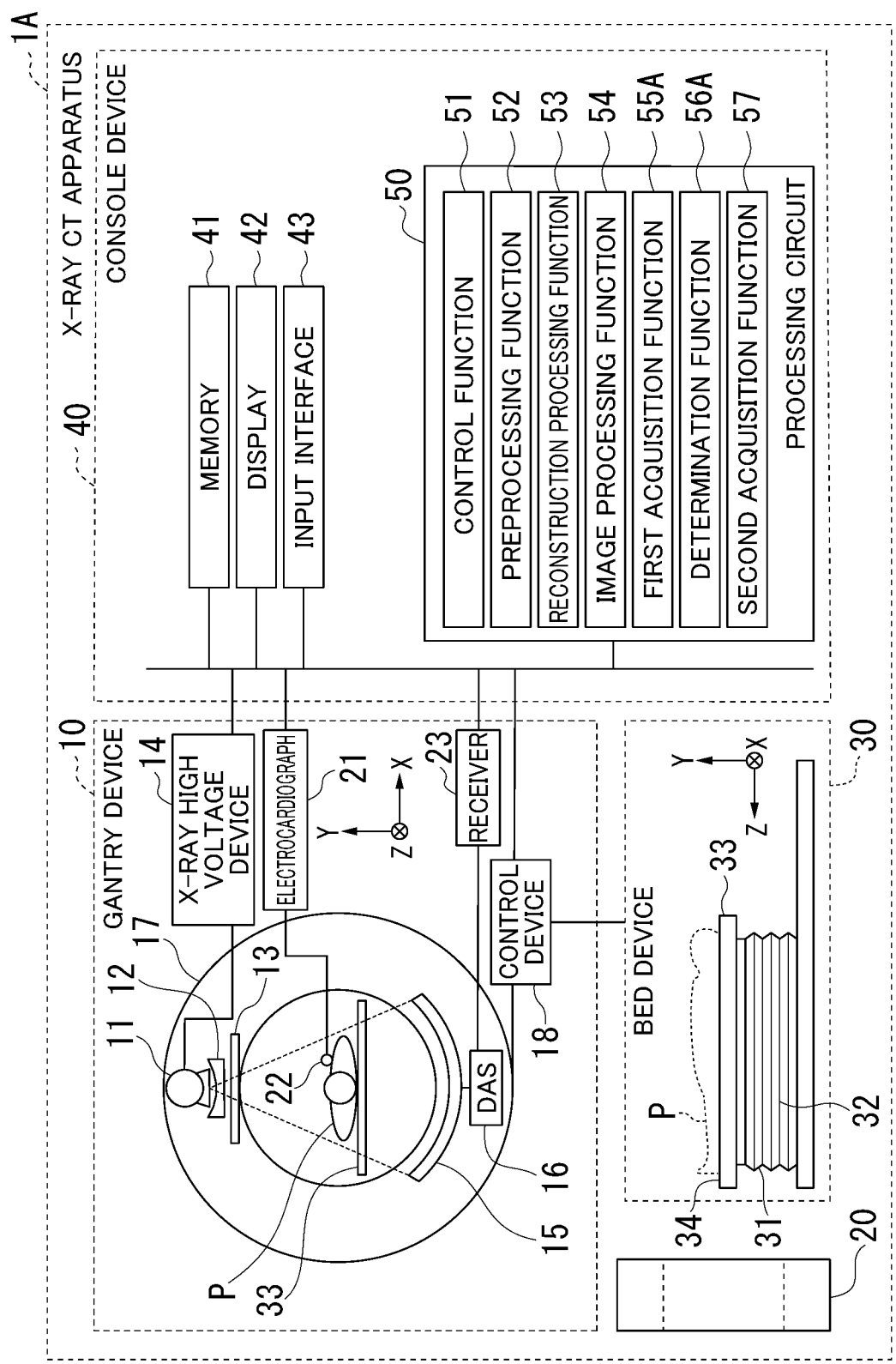
FIG. 1 is a diagram showing a configuration example of an X-ray CT apparatus according to a first embodiment.

FIG. 1 is a diagram showing a configuration example of an X-ray CT apparatus 1A according to a first embodiment. The X-ray CT apparatus 1A includes, for example, a gantry device 10, a bed device 30, and a console device 40. In FIG. 1, both a diagram of the gantry device 10 viewed in a Z-axis direction and a diagram viewed in an X-axis direction are shown for convenience of description, but in reality, there is one gantry device 10. In the embodiment, the axis of rotation of a rotating frame 17 in a non-tilted state or the longitudinal direction of a top plate 33 of the bed device 30 is defined as the Z-axis direction, an axis orthogonal to the Z-axis direction and horizontal to the floor surface is defined as the X-axis direction, and a direction orthogonal to the Z-axis direction and perpendicular to the floor surface is defined as a Y-axis direction. The X-ray CT apparatus 1A captures a contrast-enhanced CT image (hereinafter, simply referred to as a "CT image") for performing image diagnosis according to electrocardiographic synchronous helical scanning. Electrocardiographic synchronous helical scanning is an example of "biometric information synchronous scanning."

The gantry device 10 includes, for example, an X-ray tube 11, a wedge 12, a collimator 13, an X-ray high voltage device 14, an X-ray detector 15, a data acquisition system (hereinafter, DAS) 16, the rotating frame 17, a control device 18, and an electrocardiograph 21.

The X-ray tube 11 generates X-rays by radiating thermoelectrons from a cathode (filament) toward an anode (target) according to application of a high voltage from the X-ray high voltage device 14. The X-ray tube 11 includes a vacuum tube. For example, the X-ray tube 11 is a rotating anode type X-ray tube that generates X-rays by radiating thermoelectrons to a rotating anode.

The wedge 12 is a filter for adjusting an X-ray dose radiated from the X-ray tube 11 to a subject P that is an image diagnosis target. The wedge 12 attenuates X-rays passing through the wedge 12 such that a distribution of the X-ray dose applied to the subject P from the X-ray tube 11 becomes a predetermined distribution. The wedge 12 is also called a wedge filter or a bow-tie filter. The wedge 12 is made by processing aluminum to have a predetermined target angle and a predetermined thickness, for example.

The collimator 13 is a mechanism for narrowing a radiation range of X-rays that have passed through the wedge 12. The collimator 13 narrows the X-ray radiation range by forming a slit, for example, by combining a plurality of lead plates. The collimator 13 may be called an X-ray diaphragm.

The narrowing range of the collimator 13 may be mechanically driven.

The X-ray high voltage device 14 includes, for example, a high voltage generation device and an X-ray control device. The high voltage generation device has an electric circuit including a transformer, a rectifier, and the like and generates a high voltage to be applied to the X-ray tube 11. The X-ray control device controls the output voltage of the high voltage generation device according to X-ray dose to be generated in the X-ray tube 11. The high voltage generation device may be one that boosts a voltage by the transformer described above or may be one that boosts a voltage by an inverter.

The X-ray high voltage device 14 may be provided on the rotating frame 17 or may be provided on the side of a fixed frame (not shown) of the gantry device 10.

The X-ray detector 15 detects the intensity of X-rays that are generated by the X-ray tube 11, and have passed through and are incident on the subject P. The X-ray detector 15 outputs an electric signal (which may be an optical signal or the like) depending on the detected intensity of X-rays to the DAS 16. The X-ray detector 15 includes, for example, a plurality of X-ray detection element strings. Each of the plurality of X-ray detection element strings is an arrangement of a plurality of X-ray detection elements in a channel direction along an arc having a focal point of the X-ray tube 11 as a center. The plurality of X-ray detection element strings is arranged in a slice direction (column direction and row direction).

The X-ray detector 15 is an indirect detector having, for example, a grid, a scintillator array, and an optical sensor array. The scintillator array has a plurality of scintillators. Each scintillator has a scintillator crystal. The scintillator crystal emits an amount of light corresponding to the intensity of incident X-rays. The grid is disposed on the surface of the scintillator array on which X-rays are incident and has an X-ray shielding plate having a function of absorbing scattered X-rays. The grid may also be called a collimator (one-dimensional collimator or two-dimensional collimator). The optical sensor array includes, for example, an optical sensor such as a photomultiplier tube (PMT). The optical sensor array outputs an electric signal depending on the amount of light emitted by the scintillator. The X-ray detector 15 may be a direct conversion type detector having a semiconductor element that converts incident X-rays into an electric signal.

The DAS 16 includes, for example, an amplifier, an integrator, and an A/D converter. The amplifier performs amplification processing on the electric signal output by each X-ray detection element of the X-ray detector 15. The integrator integrates the amplified electrical signal over a view period. The A/D converter converts an electric signal indicating the integration result into a digital signal. The DAS 16 outputs detection data of the X-ray detector 15 based on the digital signal to the console device 40. Since X-rays are intermittently exposed in electrocardiographic synchronous helical scanning, the detection data output by the DAS 16 includes data indicating X-ray detection and data indicating X-ray non-detection (refer to FIG. 4).

The rotating frame 17 supports the X-ray tube 11, the wedge 12, the collimator 13, and the X-ray detector 15 in a facing manner. The rotating frame 17 is an annular member including both side surfaces of a circle having a circular opening formed at the center, an inner surface connecting the inner circles of both side surfaces, and an outer surface connecting the outer circles of both side surfaces. Both side surfaces of the rotating frame 17 are flat surfaces, and the inner and outer surfaces are curved surfaces.

The rotating frame 17 is an annular member that supports the X-ray tube 11, the wedge 12, the collimator 13, and the X-ray detector 15 in a facing manner. The rotating frame 17 is rotatably supported around the subject P introduced inside by a fixed frame (not shown). The rotating frame 17 further supports the DAS 16. Detection data output by the DAS 16 is transmitted from a transmitter having a light emitting diode (LED) provided in the rotating frame 17 to a receiver 23 having a photodiode provided in a non-rotating part (for example, a fixed frame) of the gantry device 10 through optical communication and transferred to the console device 40 by the receiver 23. The receiver 23 includes a memory that stores the detection data received from the transmitter at least until it is transferred to the console device 40. The method of transmitting the detection data from the rotating frame 17 to the non-rotating part is not limited to the aforementioned method using optical communication, and any non-contact transmission method may be adopted. The rotating frame 17 is not limited to an annular member as long as it can support and rotate the X-ray tube 11 and the like and may be a member such as an arm.

Although the X-ray CT apparatus 1A is, for example, a rotate/rotate-type X-ray CT apparatus (third generation CT) in which both the X-ray tube 11 and the X-ray detector 15 are supported by the rotating frame 17 and rotate around the subject P, it is not limited thereto and may be a stationary/rotate-type X-ray CT apparatus (fourth generation CT) in which a plurality of X-ray detection elements arranged in an annular shape are fixed to a fixed frame and the X-ray tube 11 rotates around the subject P.

The control device 18 includes, for example, a processing circuit having a processor such as a central processing unit (CPU) and a drive mechanism including a motor, an actuator, and the like. The processing circuit realizes these functions by, for example, a hardware processor executing a program stored in a storage device (storage circuit).

The hardware processor is, for example, a circuit (circuitry) such as a central processing unit (CPT), a graphics processing unit (GPU), an application specific integrated circuit (ASIC), a programmable logic device (for example, a simple programmable logic device (SPLD) or a complex programmable logic device (CPLD)), or a field programmable gate array (FPGA). The program may be configured to be embedded directly in the circuit of the hardware processor instead of being stored in the storage device. In this case, the hardware processor realizes a function by reading and executing the program embedded in the circuit. The hardware processor is not limited to a single circuit and may be configured as one hardware processor by combining a plurality of independent circuits to realize each function. The storage device may be a (hardware) non-transitory storage medium. A plurality of components may be integrated into one hardware processor to realize each function.

For example, the control device 18 rotates the rotating frame 17, tilts a gantry of the gantry device 10, moves the top plate 33 of the bed device 30 by vertical movement or the like, and causes the X-ray tube 11 to emit (expose) X-rays. The control device 18 may be provided in the gantry device 10 or in the console device 40.

The electrocardiograph 21 detects a weak current generated according to excitement of the heart of the subject P through a probe 22. The electrocardiograph 21 outputs temporal changes in the detected current as an electrocardiogram. The electrocardiogram is an example of "biometric information." The electrocardiogram is used to determine timing when the X-ray CT apparatus 1A exposes X-rays in electrocardiographic synchronous helical scanning of the subject P. The electrocardiogram is used to determine data (hereinafter referred to as "priority data") of a target for which data transfer to the receiver 23 or the console device 40 is preferentially performed among detection data acquired according to electrocardiographic synchronous helical scanning.

Figure 2:
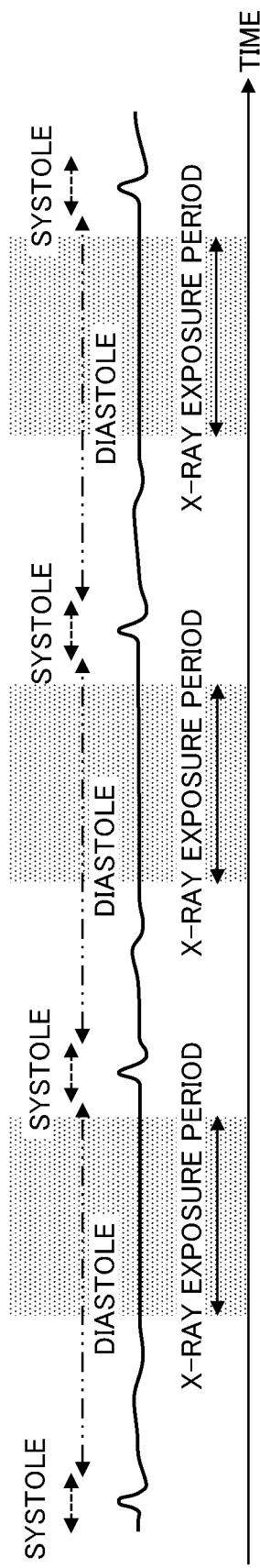
FIG. 2 is a diagram showing an example of an electrocardiogram.

FIG. 2 is a diagram showing an example of an electrocardiogram. On the electrocardiogram, characteristic waveforms such as P waves, Q waves, R waves, S waves, and T waves appear in a heartbeat cycle. FIG. 2 shows an example of the most characteristic R-wave electrocardiogram. In R waves, a systole in which the heart contracts comes after a nearly constant time. This systole is followed by a diastole in which the heart expands. These systoles and diastoles are periods in which the size of the heart drastically changes. The period from immediately after a diastole to immediately before a systole of the next heartbeat cycle is a period in which changes in the size of the heart are relatively mild, which is called an equal amount diastole.

Electrocardiographic synchronous helical scanning is a scanning method for acquiring projection data at a timing when temporal changes in electrocardiographic waveforms are small during this relaxation period. Electrocardiographic synchronous helical scanning includes a method of collecting projection data at corresponding timing from projection data acquired at a plurality of phases, a method of determining an intermittent X-ray exposure period (hereinafter referred to as an "X-ray exposure period") at corresponding timings and exposing the subject P to X-rays during the X-ray exposure period, and the like. In either case, an electrocardiogram is acquired at the time of scanning the subject P. and projection data necessary for reconstruction is identified based on electrocardiographic waveforms indicated by the acquired electrocardiogram.

Since the X-ray exposure period may differ depending on the individual subject P or the state of the subject P at the time of examination, an electrocardiogram of the subject P may be acquired before scanning is performed and the X-ray exposure period may be determined based on the acquired electrocardiogram at the time of determining the X-ray exposure period. Here, an electrocardiogram acquired before scanning is performed is referred to as a "pre-scan electrocardiogram" in order to distinguish it from an electrocardiogram acquired at the time of performing scanning. Although a preliminary electrocardiogram may be acquired at any time before the start of scanning, it is desirable to acquire it at the timing of breathing exercises performed in a conventional examination procedure, or the like in consideration of avoiding a decrease in examination efficiency. In the present embodiment, it is assumed that the X-ray exposure period is set in a sufficiently wide range such that it includes at least a priority period which will be described later. A heartbeat cycle is an example of a "biological motion cycle." Although electrocardiographic synchronous helical scanning when the X-ray exposure period is set will be exemplified below, a method of determining the priority period in the first embodiment is also applicable to electrocardiographic synchronous helical scanning when the X-ray exposure period is not set.

Return to description of FIG. 1. The bed device 30 is a device that introduces the subject P that is a scanning target into the inside of the rotating frame 17 of the gantry device 10 by carrying and moving the subject P. The bed device 30 includes, for example, a base 31, a bed driving device 32, the top plate 33, and a support frame 34.

The base 31 includes a housing that movably supports the support frame 34 in the vertical direction (Y-axis direction). The bed driving device 32 includes a motor and an actuator. The bed driving device 32 moves the top plate 33 on which the subject P is placed along the support frame 34 in the longitudinal direction (Z-axis direction) of the top plate 33. The top plate 33 is a plate-shaped member on which the subject P is placed. The bed driving device 32 retracts the top plate 33 and inserts it into an opening of the gantry 20. The bed driving device 32 advances the top plate 33 and pulls it out from the gantry 20.

The bed driving device 32 may move not only the top plate 33 but also the support frame 34 in the longitudinal direction of the top plate 33. In contrast to this, the gantry device 10 may be movable in the Z-axis direction, and the rotating frame 17 may be controlled to come around the subject P according to the movement of the gantry device 10. Both the gantry device 10 and the top plate 33 may be movable.

The console device 40 includes, for example, a memory 41, a display 42, an input interface 43, and a processing circuit 50. Although the console device 40 will be described as a separate body from the gantry device 10 in embodiments, the gantry device 10 may include some or all components of the console device 40. The console device 40 is an example of a "terminal device."

The memory 41 is realized by, for example, a random access memory (RAM), a semiconductor memory element such as a flash memory, a hard disk, an optical disc, or the like. The memory 41 stores, for example, detection data, projection data, reconstructed image data, CT image data, and the like. This data may be stored in an external memory with which the X-ray CT apparatus 1A can communicate instead of the memory 41 (or in addition to the memory 41). The external memory is controlled by, for example, a cloud server that manages the external memory when the cloud server receives a read/write request.

The display 42 displays various types of information. For example, the display 42 displays a medical image (CT image) generated by the processing circuit, an electrocardiogram output by the electrocardiograph 21, a graphical user interface (GUI) image through which various operations by an operator such as a doctor or an engineer are received, and the like. The display 42 is, for example, a liquid crystal display, a cathode ray tube (CRT), an organic electroluminescence (EL) display, or the like. The display 42 may be provided on the gantry device 10. The display 42 may be a desktop type or a display device (for example, a tablet terminal) capable of wirelessly communicating with the main body of the console device 40.

The input interface 43 receives various input operations performed by an operator and outputs an electric signal indicating the content of the received input operations to the processing circuit 50. For example, the input interface 43 receives an input operation of converting generated CT image data into three-dimensional image data or cross-sectional image data of an arbitrary cross section as an input to the image processing function 54 which will be described later.

The input interface 43 receives an operation of inputting various conditions (a scanning plan) when generating a CT image of the subject P, such as collection conditions when collecting detection data or projection data, reconstruction conditions when reconstructing a CT image, and image processing conditions when generating a post-processed image from a CT image, for example. The input interface 43 receives an operation of inputting transfer conditions when transferring detection data to the console device 40, for example.

For example, the input interface 43 receives an operation of inputting phase information as a detection data transfer condition. The phase information is information related to a heartbeat cycle and is, for example, information indicating a specific phase in the heartbeat cycle of the subject P or information indicating a section (specific section) before and after the specific phase. The phase information is used to determine priority data from detection data acquired through electrocardiographic synchronous helical scanning.

Figure 3:
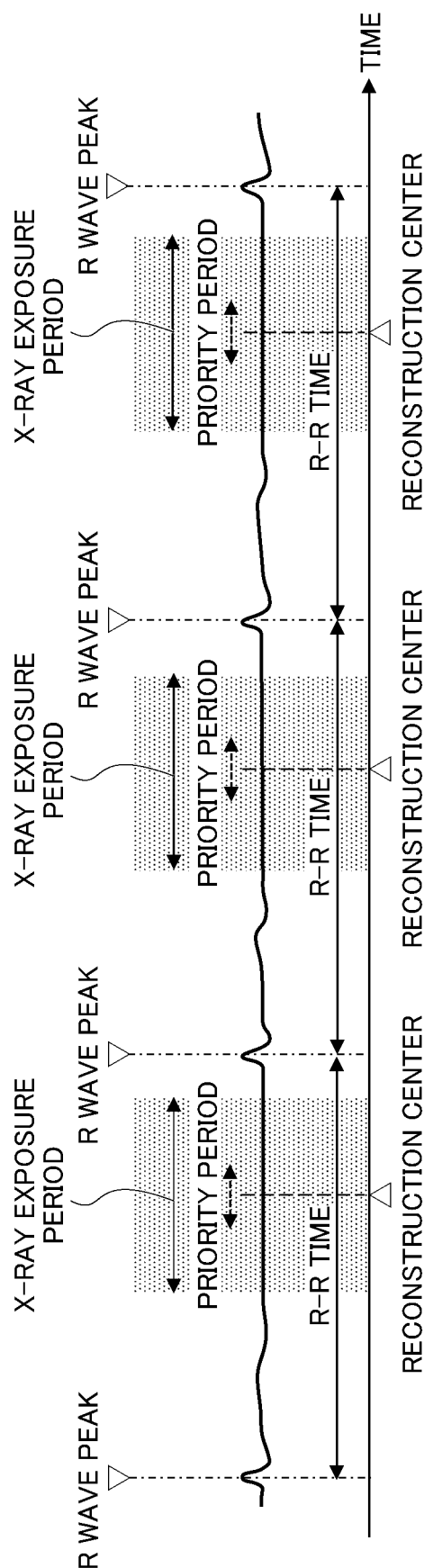
FIG. 3 is a diagram showing an example of a method of determining priority data based on phase information.

FIG. 3 is a diagram showing an example of a method of determining priority data based on phase information. The example of an electrocardiogram shown in FIG. 3 is the same as that shown in FIG. 2. Generally, in electrocardiographic synchronous helical scanning, a target phase (reconstruction center) of reconstruction processing is about 75% of R-R time (a time width between adjacent R wave peaks), and projection data of a period of about 5% before and after the reconstruction center (that is, a period of 70% to 80%) is required in order to generate a CT image of the reconstruction center. The example of FIG. 3 is an example of a case in which the reconstruction center and a priority data acquisition period (hereinafter referred to as a "priority period") are determined based on this idea.

In this case, the input interface 43 is configured to receive an operation of inputting a value "75%" indicating the reconstruction center and a value "5%" indicating the width of the priority period as phase information. The reconstruction center and the priority period are determined based on an electrocardiogram acquired during scanning (hereinafter referred to as "scanning electrocardiogram").

For example, the input interface 43 may be configured to receive an input operation for causing the display 42 to display a scanning electrocardiogram and designating a reconstruction center and a priority period for the displayed scanning electrocardiogram. Temporal changes in the R wave may differ for each heartbeat cycle. Therefore, the input interface 43 may be configured to receive an input operation for designating a reconstruction center and a priority period for each heartbeat cycle.

The input interface 43 is realized by, for example, a mouse, a keyboard, a touch panel, a track ball, a switch, a button, a joystick, a camera, an infrared sensor, a microphone, or the like. The input interface 43 may be realized by a display device (for example, a tablet terminal) capable of wirelessly communicating with the main body of the console device 40.

In the present description, the input interface 43 is not limited to the one provided with physical operation parts such as a mouse and a keyboard. For example, examples of the input interface 43 include an electric signal processing circuit that receives an electric signal corresponding to an input operation from an external input device provided separately from the device and outputs the electric signal to a control circuit. The input interface 43 is an example of an "input unit."

Return to description of FIG. 1. The processing circuit 50 controls the overall operation of the X-ray CT apparatus 1A. The processing circuit 50 includes, for example, a control function 51, a preprocessing function 52, a reconstruction processing function 53, an image processing function 54, a first acquisition function 55A, a determination function 56A, and a second acquisition function 57. The processing circuit 50 realizes these functions by, for example, a hardware processor executing a program stored in a storage device (storage circuit).

The hardware processor means, for example, a circuit such as a CPU, a GPU, an integrated circuit for a specific application, a programmable logic device or a composite programmable logic device, or a field programmable gate array. The program may be directly embedded in the circuit of the hardware processor instead of being stored in the storage device. The hardware processor is not limited to the one configured as a single circuit and may be configured as one hardware processor by combining a plurality of independent circuits to realize each function. The storage device may be a (hardware) non-transitory storage medium. A plurality of components may be integrated into one hardware processor to realize each function.

Components included in the console device 40 or the processing circuit 50 may be decentralized and realized by a plurality of hardware devices. The processing circuit 50 may be realized by a processing device capable of communicating with the console device 40 instead of being a component included in the console device 40. The processing device is, for example, a workstation connected to one X-ray CT apparatus, or a device (e.g., a cloud server) connected to a plurality of X-ray CT apparatuses and collectively executing the same processing as that of the processing circuit 50 which will be described below.

Each function included in the processing circuit 50 may be distributed to a plurality of circuits or may be configured to be available by activating application software stored in the memory 41. For example, the control function 51, the preprocessing function 52, the reconstruction processing function 53, and the image processing function 54 are included in the processing circuit 50, and the first acquisition function 55A, the determination function 56A, and the second acquisition function 57 may be configured to be available by activating application software stored in the memory 41.

The control function 51 controls various functions of the processing circuit 50 based on an input operation received by the input interface 43. For example, the control function 51 stores an input scanning plan in the memory 41 and executes scanning of the subject P according to the scanning plan stored in the memory 41. For example, the control function 51 executes detection data collection processing in the gantry device 10, and the like by controlling the X-ray high voltage device 14, the DAS 16, the control device 18, and the bed driving device 32.

The preprocessing function 52 generates projection data by performing preprocessing (logarithmic conversion processing, offset correction processing, interchannel sensitivity correction processing, beam hardening correction, and the like) on detection data output by the DAS 16 according to the scanning plan and stores the generated projection data in the memory 41.

The reconstruction processing function 53 generates CT image data by performing reconstruction processing (according to a filter correction back projection method, a sequential approximation reconstruction method, and the like) on the projection data generated by the preprocessing function 52 according to the scanning plan and stores the generated CT image data in the memory 41.

The image processing function 54 converts the CT image data into three-dimensional image data or cross-sectional image data of an arbitrary cross section by a known method based on an input operation received by the input interface 43. Conversion into the three-dimensional image data may be performed by the preprocessing function 52.

The first acquisition function 55A acquires a scanning electrocardiogram and stores the electrocardiogram in the memory 41.

The determination function 56A determines priority data from detection data acquired through electrocardiographic synchronous helical scanning based on the scanning electrocardiogram. Specifically, the determination function 56A determines, as the priority data, detection data acquired in a priority period determined based on the scanning electrocardiogram in a period in which electrocardiographic synchronous helical scanning is performed. The determination function 56A instructs the second acquisition function 57 to acquire the determined priority data.

The second acquisition function 57 acquires the detection data acquired by performing electrocardiographic synchronous helical scanning on the subject P from the gantry device 10 and stores the acquired detection data in the memory 41. The detection data acquired by the second acquisition function 57 is used to generate projection data by the preprocessing function 52. Then, the reconstruction processing function 53 performs reconstruction processing using the projection data generated by the preprocessing function 52 to generate a CT image.

Figure 4:
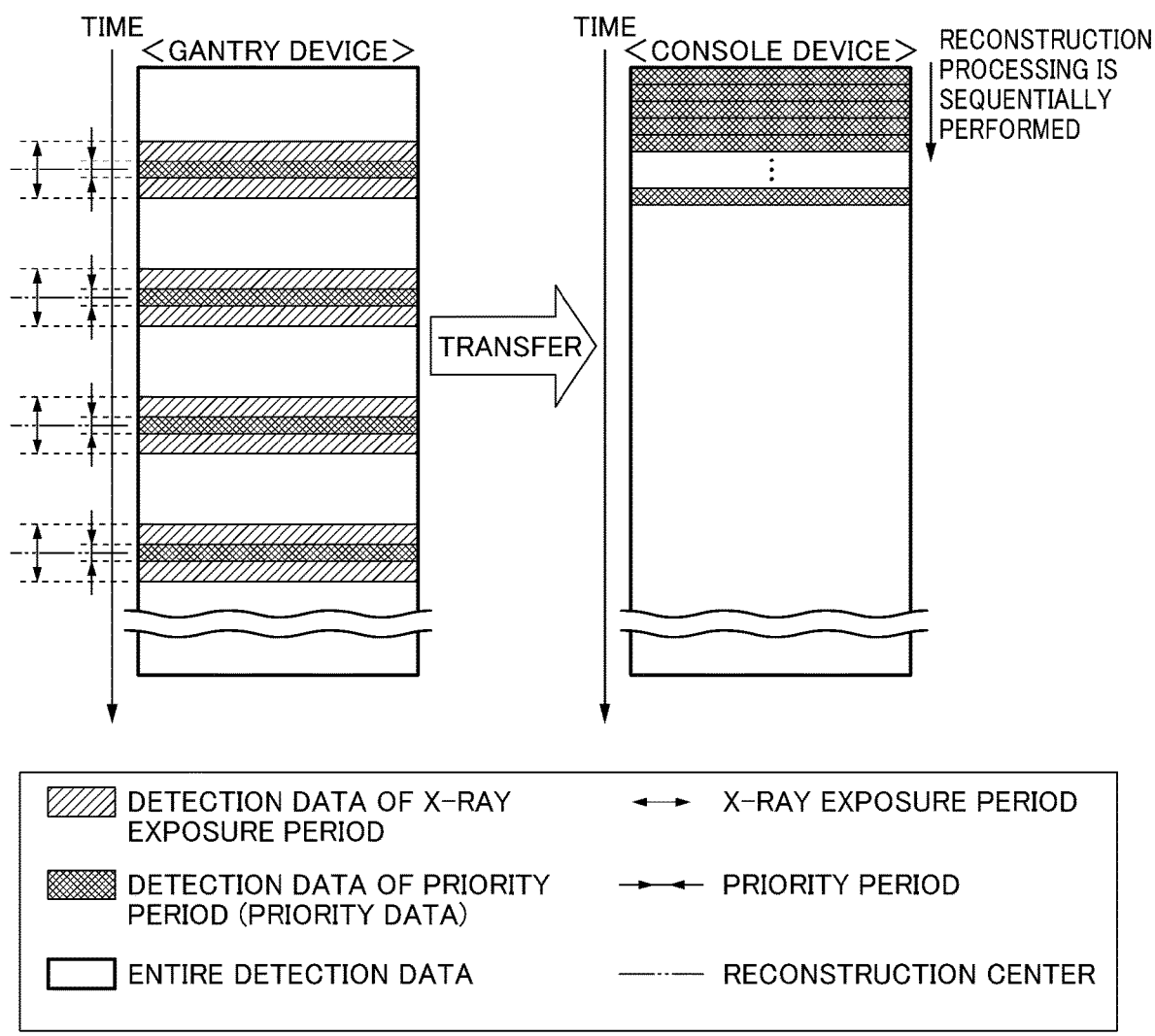
FIG. 4 is an image diagram showing a method of transferring X-ray CT apparatus priority data of the first embodiment from a gantry device to a console device.

FIG. 4 is an image diagram showing a method in which the X-ray CT apparatus 1A of the first embodiment transfers priority data from the gantry device 10 to the console device 40. Although the gantry device 10 exposes X-rays in each discretely set X-ray exposure period in electrocardiographic synchronous helical scanning, as described above, the DAS 16 outputs a signal indicating that X-rays are not detected even at a timing when X-rays are not exposed during scanning. Accordingly, detection data indicating that X-rays have been detected (data in a non-blank portion in the figure, which becomes projection data by preprocessing) and detection data indicating that X-rays have not been detected (data in a blank portion in the figure) are alternately included in detection data output by the DAS 16, as shown in FIG. 4.

In this case, the determination function 56A recognizes a priority period based on phase information input through the input interface 43 and determines detection data acquired in the priority period as priority data. The determination function 56A instructs the second acquisition function 57 to acquire the determined priority data from the gantry device 10. Specifically, the determination function 56A notifies the second acquisition function 57 of the recognized priority period, and the second acquisition function 57 acquires the detection data of the notified priority period from the gantry device 10 in the order in which the detection data is acquired.

The determination function 56A may be configured to acquire all priority data among all acquired detection data and then acquire a part or all of the remaining detection data (hereinafter referred to as "non-priority data") from the gantry device 10. For example, in the example of FIG. 4, non-priority data is detection data other than priority data among detection data of an X-ray exposure period, and detection data indicating that X-rays have not been detected.

As a result, the console device 40 can shorten a waiting time until detection data required for reconstruction processing is transferred and can rapidly start reconstruction processing. Specifically, reconstruction processing is started after waiting for the entire detection data to be transferred to the console device 40 conventionally, whereas reconstruction processing can be started after waiting for a time required for priority data transfer according to the transfer method of the present embodiment.

Although a case in which the second acquisition function 57 acquires all priority data from the gantry device 10 among all the acquired detection data and then acquires a part or all of non-priority data from the gantry device 10 has been described in the example of FIG. 4, the second acquisition function 57 may be configured to acquire all the priority data from the gantry device 10 and then delete a part or all of the non-priority data from the gantry device 10. For example, the second acquisition function 57 may instruct the gantry device 10 to delete the non-priority data based on an input operation of a user or may instruct the gantry device 10 to delete the non-priority data based on preset conditions regarding handling of the non-priority data, and the like.

Figure 5:
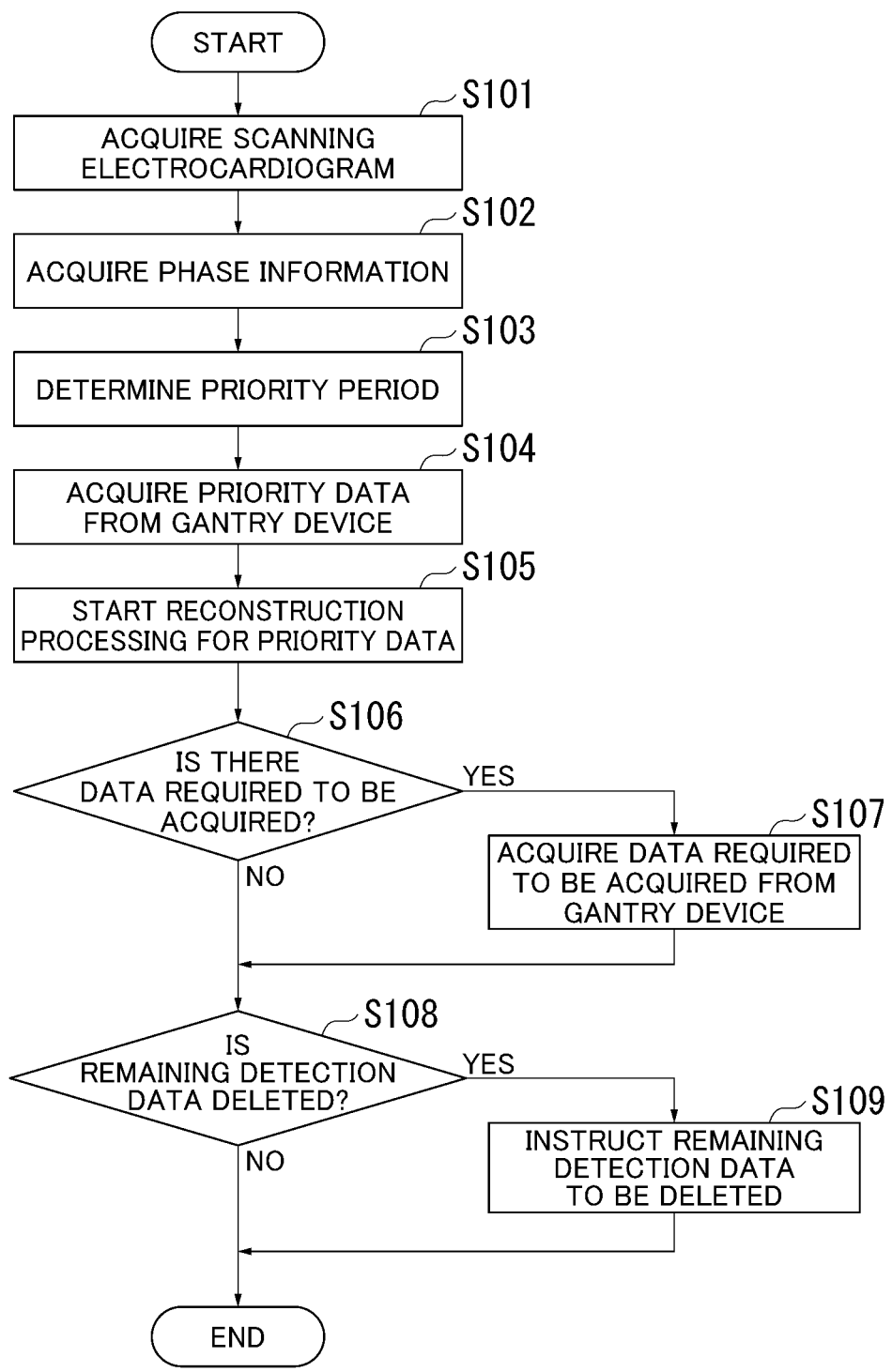
FIG. 5 is a flowchart showing an example of a flow of processing in which the X-ray CT apparatus determines priority data.

FIG. 5 is a flowchart showing an example of a flow of processing in which the X-ray CT apparatus 1A determines priority data. The processing flow shown in FIG. 5 is started after scanning of the subject P according to electrocardiographic synchronous helical scanning is completed, that is, after detection data with respect to the subject P is acquired by the gantry device 10. First, the first acquisition function 55A acquires a scanning electrocardiogram from the electrocardiograph 21 and stores the scanning electrocardiogram in the memory 41 (step S101).

Subsequently, the determination function 56A acquires phase information for determining priority data from detection data acquired by the gantry device 10 via the input interface 43 (step S102). The determination function 56A stores the acquired phase information in the memory 41. The determination function 56A determines a priority period based on the acquired scanning electrocardiogram and the phase information (step S103).

Subsequently, the second acquisition function 57 acquires detection data acquired in the priority period determined by the determination function 56A from the gantry device 10 as priority data (step S104) and stores the acquired priority data in the memory 41. When the priority data is acquired from the gantry device 10, the preprocessing function 52 performs preprocessing on the acquired priority data, and the reconstruction processing function 53 starts reconstruction processing using the preprocessed priority data. Here, it is assumed that the gantry device 10 deletes detection data transferred to the console device 40 from the gantry device 10 after transfer of the detection data is completed.

Subsequently, the second acquisition function 57 determines whether or not there is detection data (hereinafter referred to as "data required to be acquired") to be acquired by the console device 40 among detection data (non-priority data) other than the priority data (step S105). For example, the second acquisition function 57 causes the display 42 to display a display indicating that data required to be acquired can be designated and receives an input of an operation for designating data required to be acquired via the input interface 43. In this case, the second acquisition function 57 determines that "there is data required to be acquired" when the operation for designating data required to be acquired is input and determines that "there is no data required to be acquired" when the operation for designating data required to be acquired is not input. For example, the second acquisition function 57 may determine presence or absence of data required to be acquired based on conditions and the like preset with respect to data required to be acquired.

Here, if it is determined that "there is data required to be acquired" (step S105—YES), the second acquisition function 57 acquires the data required to be acquired from the gantry device 10 (step S106) and stored the acquired data required to be acquired in the memory 41. On the other hand, if it is determined that "there is no data required to be acquired" (step S106—NO), the second acquisition function 57 skips step S106 and proceeds to step S107.

Subsequently, the second acquisition function 57 determines whether or not to delete other detection data (hereinafter referred to as "unacquired data") that has not been acquired from the gantry device 10 (step S107). The second acquisition function 57 may determine whether or not to delete the unacquired data based on an input operation of a user, preset conditions, or the like, as in the case of data required to be acquired. Here, if it is determined that the unacquired data will be deleted (step S107—YES), the second acquisition function 57 instructs the gantry device 10 to delete the unacquired data (step S108). On the other hand, if it is determined that the unacquired data will not be deleted (step S07—NO), step S108 is skipped, and the processing flow ends.

According to the X-ray CT apparatus 1A of the first embodiment configured in this manner, detection data necessary for reconstruction processing can be preferentially transferred from the gantry device 10 to the console device 40, and thus reconstruction processing can be rapidly started after execution of scanning on the subject P.

Second Embodiment

Figure 6:
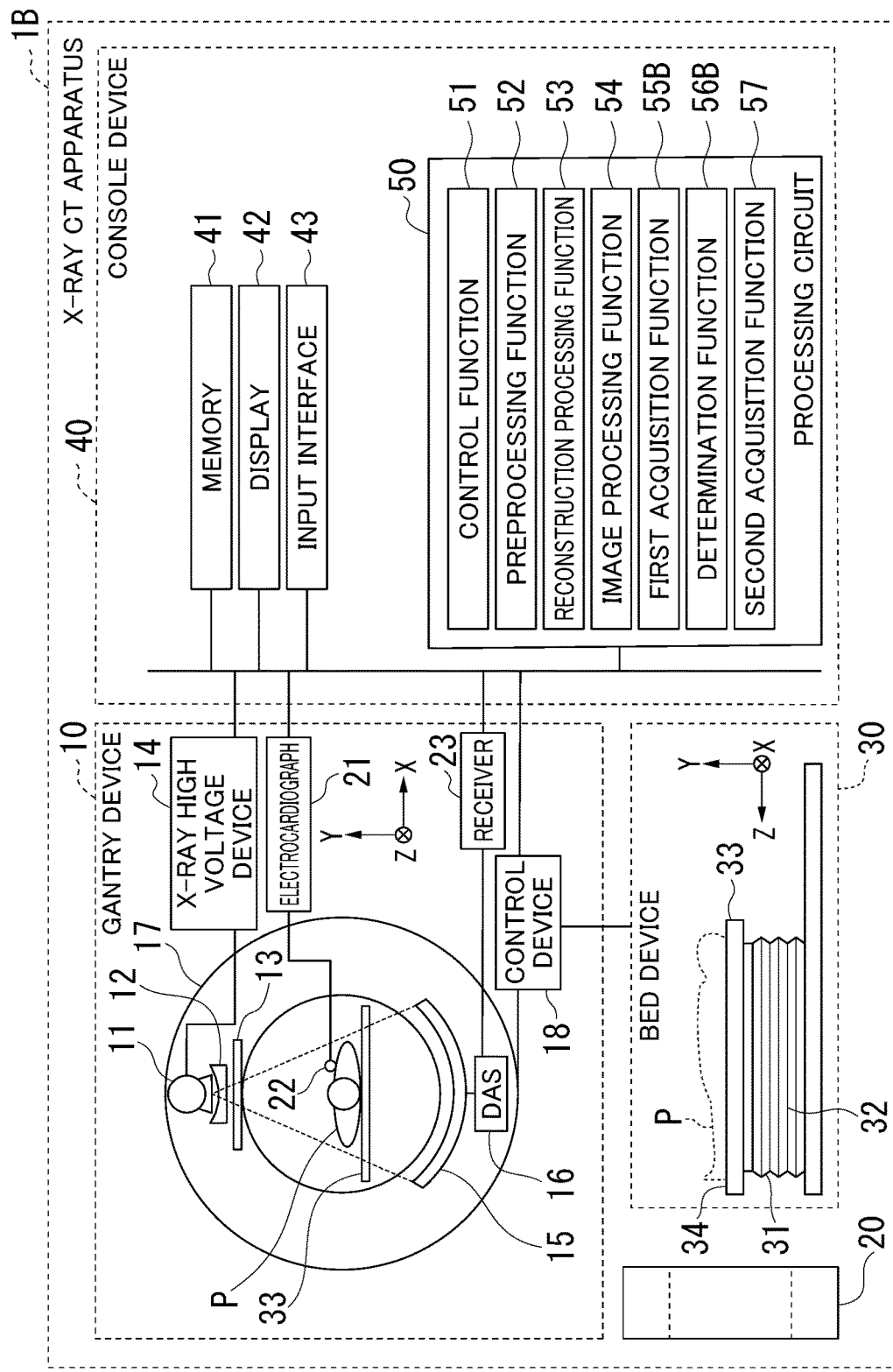
FIG. 6 is a diagram showing a configuration example of an X-ray CT apparatus according to a second embodiment.

FIG. 6 is a diagram showing a configuration example of an X-ray CT apparatus 1B according to a second embodiment. The X-ray CT apparatus 1B differs from the X-ray CT apparatus 1A of the first embodiment in that the processing circuit 50 includes a first acquisition function 55B instead of the first acquisition function 55A and the processing circuit 50 includes a determination function 56B instead of the determination function 56A. Since the other components of the X-ray CT apparatus 1B are the same as those of the X-ray CT apparatus 1A, description thereof is omitted here by assigning the same reference numerals as those in FIG. 1 to the same components as those of the X-ray CT apparatus 1A in FIG. 6.

The first acquisition function 55B differs from the first acquisition function 55A in that it acquires exposure information indicating X-ray exposure timing in electrocardiographic synchronous helical scanning instead of a scanning electrocardiogram of the subject P. The first acquisition function 55B stores the acquired exposure information in the memory 41.

The determination function 56B differs from the determination function 56A in that it determines priority data based on exposure information instead of a scanning electrocardiogram. Specifically, the determination function 56B determines, as priority data, detection data acquired in a period in which detection data indicating detection of X-rays is acquired (X-ray exposure period). This may be rephrased as that the determination function 56B sets the X-ray exposure period as a priority period. The determination function 56B instructs the second acquisition function 57 to acquire the determined priority data.

Figure 7:
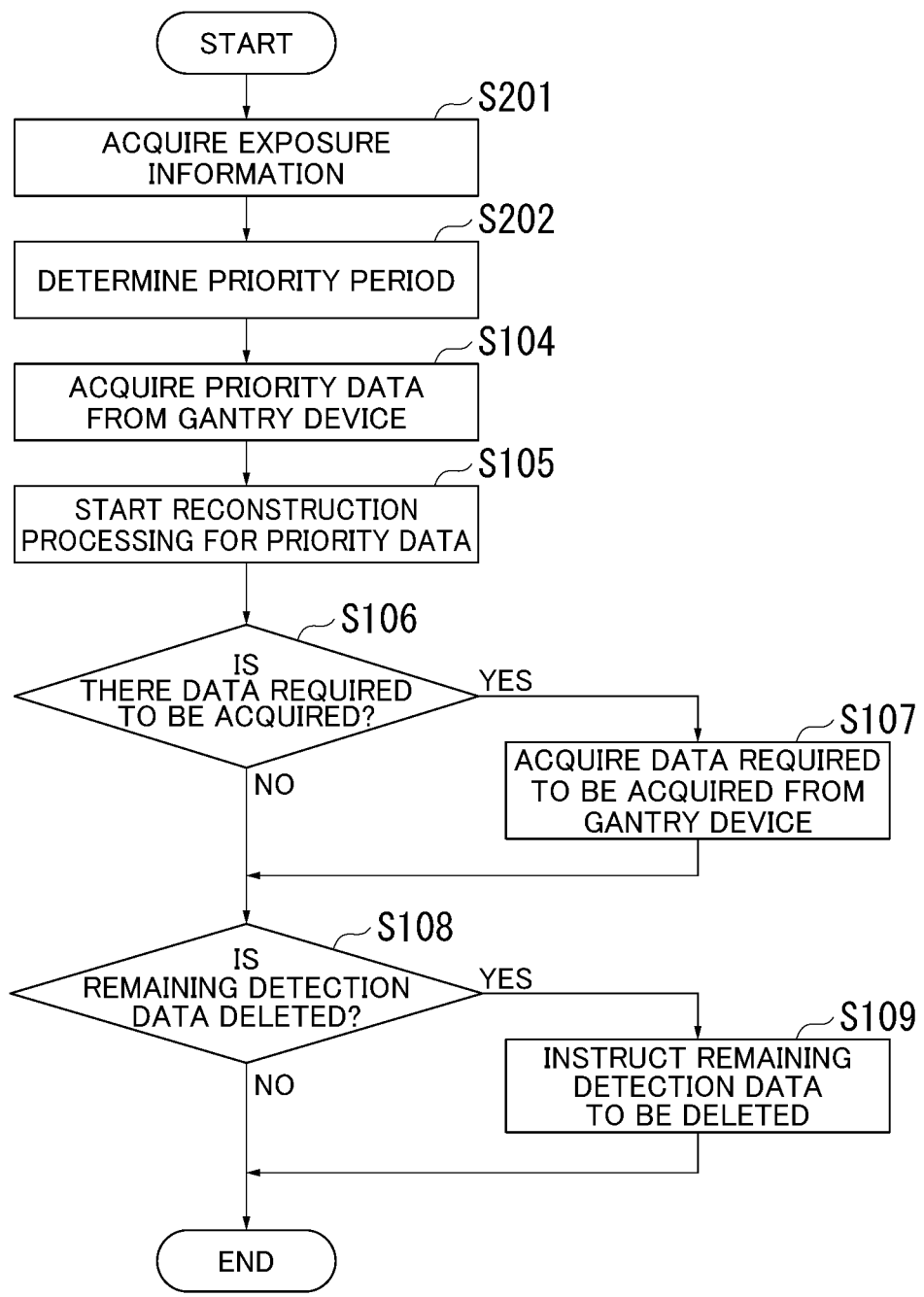
FIG. 7 is a flowchart showing an example of a flow of processing in which the X-ray CT apparatus determines priority data.

FIG. 7 is a flowchart showing an example of a flow of processing in which the X-ray CT apparatus 1B determines priority data. Among processes shown in the flowchart of FIG. 7, the same processes as those of the method of determining priority data in the first embodiment are designated by the same reference numerals as those in FIG. 5, and description thereof is omitted here. First, the first acquisition function 55B acquires exposure information indicating X-ray exposure timing in electrocardiographic synchronous helical scanning performed on the subject P (step S201).

Here, it is assumed that the control device 18 of the gantry device 10 records a timing at which X-rays are exposed at the time of performing electrocardiographic synchronous helical scanning as log information. The first acquisition function 55B acquires the log information from the control device 18, extracts exposure information from the acquired log information, and stores the exposure information in the memory 41. When the same log information as described above is stored in the memory 41 as log information of the control function 51, the first acquisition function 55B acquires the log information of the control function 51 from the memory 41 and extracts exposure information from the log information of the control function 51.

Subsequently, the determination function 56B acquires the exposure information from the memory 41 and determines a priority period based on the acquired exposure information (step S202). Specifically, the determination function 56B recognizes an X-ray exposure period in electrocardiographic synchronous helical scanning based on the exposure information and determines the recognized X-ray exposure period as a priority period.

Figure 8:
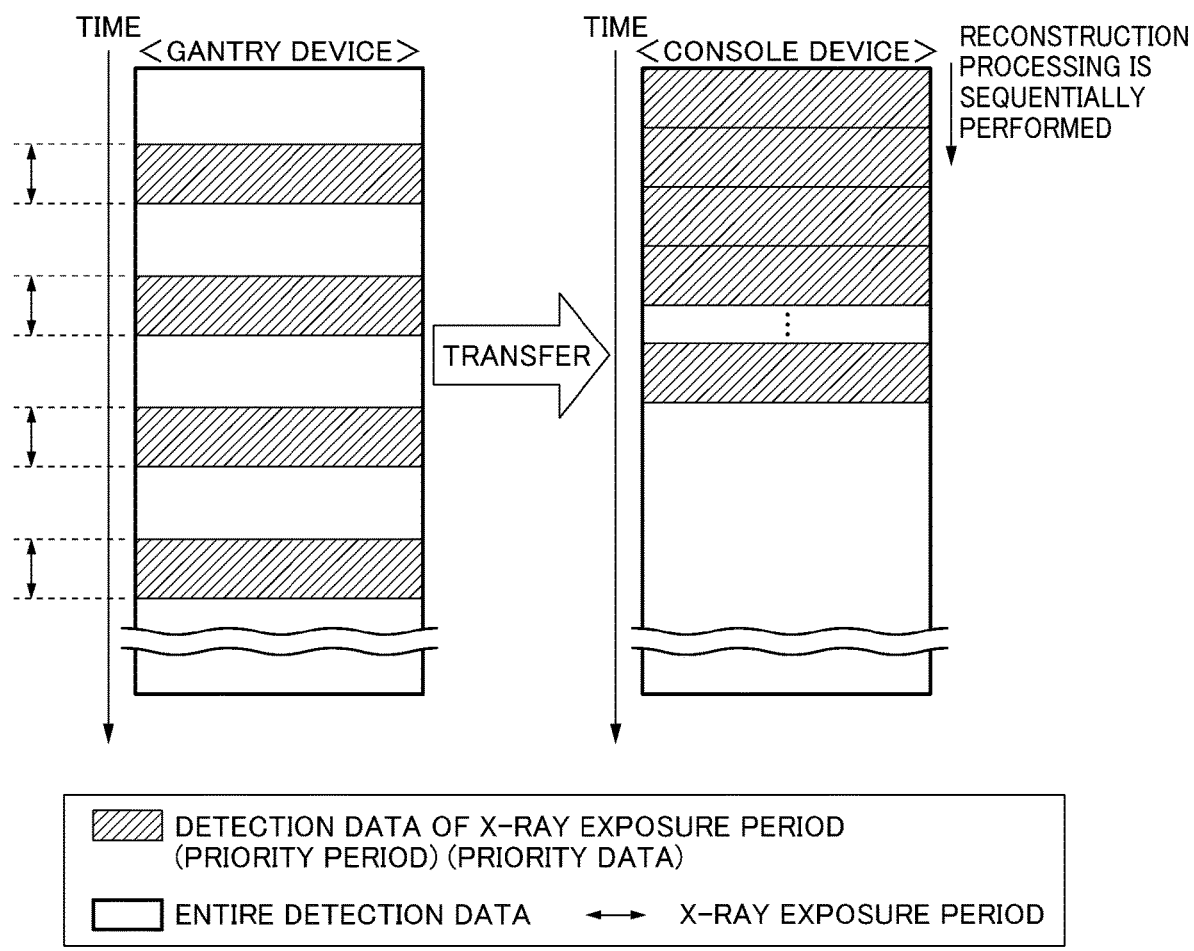
FIG. 8 is an image diagram showing a method in which the X-ray CT apparatus of the second embodiment transfers priority data from the gantry device to the console device.

In this case, the second acquisition function 57 acquires detection data acquired in the X-ray exposure period as priority data from the gantry device 10 in step S104. FIG. 8 is an image diagram showing a method in which the X-ray CT apparatus 1B of the second embodiment transfers priority data from the gantry device 10 to the console device 40. As described above, since the X-ray exposure period is set such that it includes at least a priority period in the first embodiment, the detection data of the X-ray exposure period including the priority data is transferred from the gantry device 10 to the console device 40 in the second embodiment.

According to the X-ray CT apparatus 1B of the second embodiment configured in this manner, detection data of the X-ray exposure period including priority data necessary for reconstruction processing can be preferentially transferred from the gantry device 10 to the console device 40, and thus reconstruction processing can be rapidly started after execution of scanning of the subject P.

The method of transferring detection data in the second embodiment preferentially transfers detection data of the X-ray exposure period. Accordingly, the method of transferring detection data in the second embodiment has a longer waiting time until reconstruction processing can be started than the method of transferring detection data in the first embodiment, but a priority period can be mechanically determined based on the actual X-ray exposure period and thus it is possible to shorten a waiting time until the start of reconstruction processing while simplifying the configuration with respect to determination of the priority period.

Modified Examples

Although a case in which priority data is preferentially transferred when detection data is transferred from the gantry device 10 to the console device 40 has been described in the first embodiment, this transfer method may be applied to data transfer in the gantry device 10. As described above, detection data is stored in the memory of the DAS 16 first, transmitted from the memory of the DAS 16 to the receiver 23 via the transmitter (not shown), and transferred to the console device 40 by the receiver 23. Therefore, the transfer method of the first embodiment may be applied to data transfer from the DAS 16 to the receiver 23.

Figure 9:
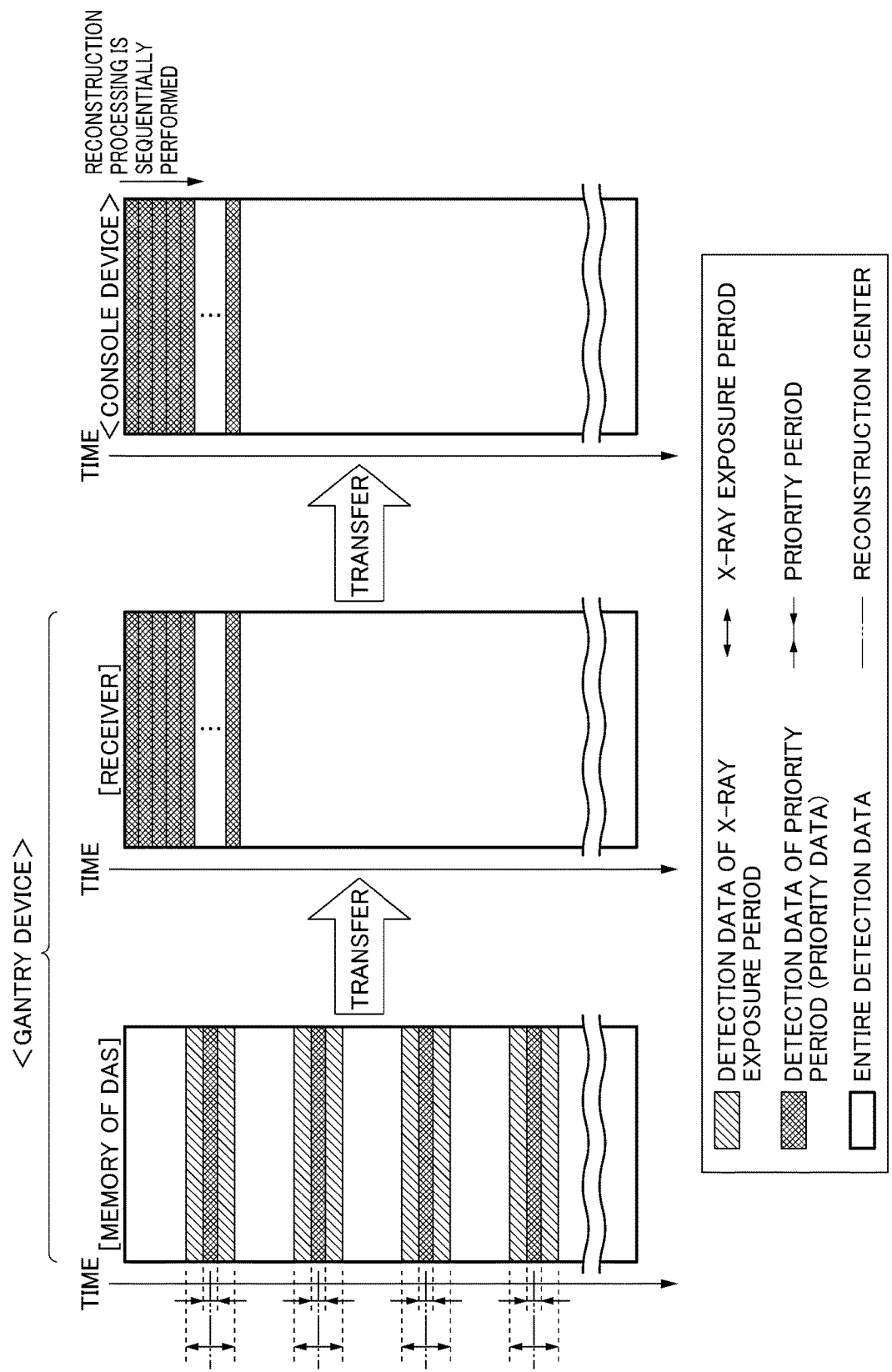
FIG. 9 is an image diagram showing a case where the transfer method of the first embodiment is applied to data transfer from a DAS 16 to a receiver 23.

FIG. 9 is an image diagram when the transfer method of the first embodiment is applied to data transfer from the DAS 16 to the receiver 23. In this case, among detection data stored in the memory of the DAS 16, priority data is preferentially transferred to the receiver 23. In this case, when a data transfer request is received from the console device 40, the receiver 23 may transfer detection data received from the DAS 16 to the console device 40 in the order of reception. In this case, the first acquisition function 55A, the determination function 56A, and the second acquisition function 57 related to determination of a priority period may be provided in the receiver 23 or the DAS 16.

Figure 10:
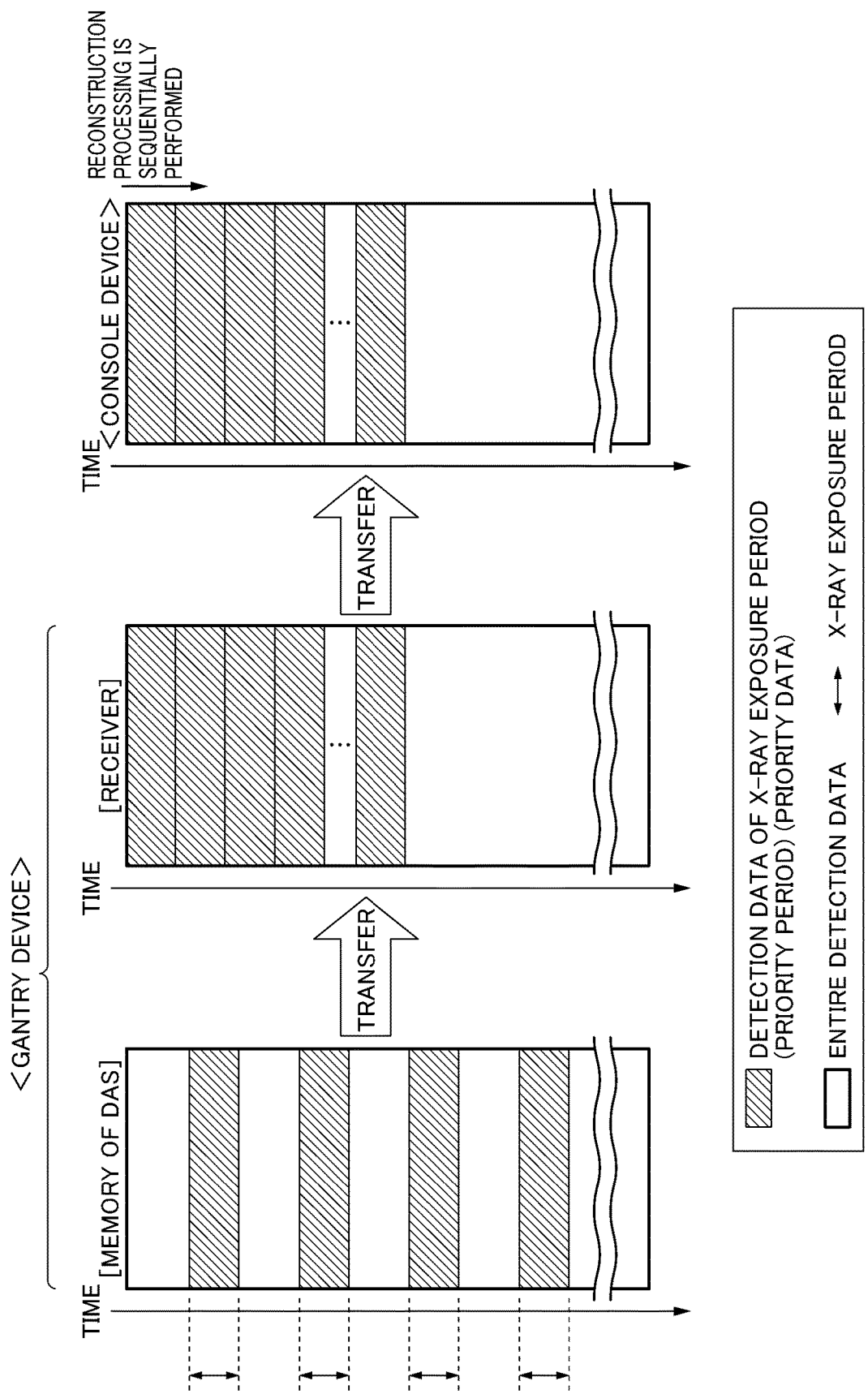
FIG. 10 is an image diagram showing a case where the transfer method of the second embodiment is applied to data transfer from the DAS 16 to the receiver 23.

Similarly to this, the transfer method of the second embodiment may be applied to data transfer from the DAS 16 to the receiver 23. FIG. 10 is an image diagram when the transfer method of the second embodiment is applied to data transfer from the DAS 16 to the receiver 23. In this case, among detection data stored in the memory of the DAS 16, priority data is preferentially transferred to the receiver 23. In this case, when a data transfer request is received from the console device 40, the receiver 23 may transfer detection data received from the DAS 16 to the console device 40 in the order of reception. In this case, the first acquisition function 55B, the determination function 56B, and the second acquisition function 57 related to determination of a priority period may be provided in the receiver 23 or the DAS 16.

Although the detection data transfer methods have been described in the first embodiment and the second embodiment, the transfer methods of the embodiments may be used as a projection data transfer method when a projection data is generated in a detection data transfer source or when detection data is used as projection data as it is. Although a case in which a transfer destination device serves as a main agent in acquiring detection data from a transfer source device has been described in the first embodiment and the second embodiment, the transfer method of the embodiments is also applicable when the transfer source device serves as a main agent in transmitting detection data to a transfer destination.

Although the embodiments of the X-ray CT apparatuses 1A and 1B (hereinafter referred to as "X-ray CT apparatus 1") have been described above, the method of transferring detection data by the X-ray CT apparatus 1 may be applied to other medical image diagnostic apparatuses. Medical image diagnostic apparatuses to which the X-ray CT apparatus can be applied may be anyone that generates a medical image by performing reconstruction processing on projection data based on detection data, and may be, for example, a positron emission tomography (PET)-CT apparatus, a magnetic resonance imaging (MRI) apparatus, an angiography imaging apparatus, and the like.

The detection data transfer method in the present embodiment is applicable to a two-stage transfer type X-ray CT apparatus that performs biometric information synchronous scanning. Biometric information synchronous scanning may be performed in synchronization with periodic biological motion of a subject. For example, biometric information synchronous scanning may be respiratory synchronous scanning performed in synchronization with the respiration of a subject, in addition to electrocardiographic synchronous scanning performed in synchronization with the heartbeat of a subject described in the above embodiment. For example, the scanning method may be helical scanning or non-helical scanning.

According to at least one embodiment described above, the X-ray CT apparatus of the embodiment can start reconstruction processing more rapidly in a two-stage transfer type X-ray CT apparatus by including a first acquisition unit that acquires biometric information of a subject at a timing when biometric information synchronous scanning has been performed, a determination unit that determines priority data among X-ray detection data acquired in biometric information synchronous scanning based on the biometric information, and a second acquisition unit that acquires priority data from a storage device that holds detection data.

While certain embodiments have been described, these embodiments have been presented by way of example only, and are not intended to limit the scope of the inventions. Indeed, the novel embodiments described herein may be embodied in a variety of other forms; furthermore, various omissions, submissions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus that acquires projection data of a subject based on X-ray detection data according to biometric information synchronous scanning and generates a CT image of the subject based on the projection data, the apparatus comprising:
   a gantry device that performs radiation and detection of X-rays in the biometric information synchronous scanning and stores the X-ray detection data acquired in the biometric information synchronous scanning on a storage device included in the gantry device; and
   processing circuitry configured to
      acquire biometric information of the subject at a timing when the biometric information synchronous scanning has been performed,
      determine, as priority data, particular detection data that is a target for which data transfer will be preferentially performed first among the X-ray detection data acquired in the biometric information synchronous scanning based on the biometric information, and acquire the determined priority data from the storage device included in the gantry device.

2. The X-ray CT apparatus according to claim 1, wherein the processing circuitry is further configured to determine, as the priority data, certain detection data acquired in a priority period determined based on the biometric information in a period in which certain the detection data has been acquired.

3. The X-ray CT apparatus according to claim 2, wherein the processing circuitry is further configured to input phase information regarding periodic biometric movement of the subject, and
   determine the priority period based on the biometric information and the phase information.

4. The X-ray CT apparatus according to claim 2, wherein the processing circuitry is further configured to acquire the certain X-ray detection data of the priority period among the detection data stored in the gantry device from the gantry device as the priority data.

5. The X-ray CT apparatus according to claim 3, wherein the phase information is information indicating a specific phase in a biological motion cycle of the subject, or information indicating a specific section before and after the specific phase, and
   the processing circuitry is further configured to determine detection data at the specific phase or detection data in the specific section as the priority data.

6. The X-ray CT apparatus according to claim 4, wherein the processing circuitry is included in a terminal device included in the X-ray CT apparatus, the terminal having a projection data reconstruction processing function, and
   the terminal device is configured to perform reconstruction processing on the priority data acquired from the gantry device by the processing circuitry.

7. The X-ray CT apparatus according to claim 4, wherein the processing circuitry is further configured to acquire all the priority data among the X-ray detection data acquired with respect to the subject from the gantry device, and then acquire some or all of the remaining X-ray detection data from the gantry device.

8. The X-ray CT apparatus according to claim 4, wherein the processing circuitry is further configured to acquire all the priority data from the gantry device, and then delete some or all of the remaining X-ray detection data based on an input operation of a user or based on preset conditions regarding handling of the non-priority data.

9. An X-ray CT apparatus that acquires projection data of a subject based on X-ray detection data according to biometric information synchronous scanning and generates a CT image of the subject based on the projection data, the apparatus comprising:
   a gantry device that performs radiation and detection of X-rays in the biometric information synchronous scanning and stores the X-ray detection data acquired in the biometric information synchronous scanning on a storage device included in the gantry device; and
   processing circuitry configured to
      acquire exposure information indicating an X-ray exposure timing in the biometric information synchronous scanning,
      determine, as priority data, particular detection data that is a target for which data transfer will be preferentially performed first among the X-ray detection data acquired in the biometric information synchronous scanning based on the exposure information, and
      acquire the determined priority data from the storage device included in the gantry device,
   wherein the X-ray detection data includes data indicating that X-rays have been detected and/or data indicating that X-rays have not been detected, and the processing circuitry is further configured to acquire the data indicating that X-rays have been detected as the priority data.

\* \* \* \* \*